(12) United States Patent
Zadig et al.

(10) Patent No.: US 10,921,244 B2
(45) Date of Patent: Feb. 16, 2021

(54) METHOD AND SYSTEM FOR MEASURING FLUID STATUS

(71) Applicant: Spectroflow, Inc., Portola Valley, CA (US)

(72) Inventors: Stephen Zadig, Portola Valley, CA (US); Dan Eric Buffkin, Jr., Newberry, FL (US); Michael Dillhyon, Miami, FL (US)

(73) Assignee: Spectroflow, Inc., Portola Valley, CA (US)

( * ) Notice: Subject to any disclaimer, the term of this patent is extended or adjusted under 35 U.S.C. 154(b) by 0 days.

(21) Appl. No.: 16/685,486

(22) Filed: Nov. 15, 2019

(65) Prior Publication Data
US 2020/0158631 A1    May 21, 2020

Related U.S. Application Data

(60) Provisional application No. 62/768,445, filed on Nov. 16, 2018.

(51) Int. Cl.
*G01N 21/359* (2014.01)
*A61B 5/00* (2006.01)

(52) U.S. Cl.
CPC ......... *G01N 21/359* (2013.01); *A61B 5/0082* (2013.01); *G01N 2201/0221* (2013.01); *G01N 2201/062* (2013.01)

(58) Field of Classification Search
CPC ..... A61B 5/0826; A61B 5/103; A61B 5/1075; A61B 5/145; A61B 5/14503; A61B 5/14507; A61B 5/14517; A61B 5/14735; A61B 5/1491; A61B 5/20; A61B 5/201; A61B 5/4064; A61B 5/416; A61B 5/42; A61B 5/4381; A61B 5/441; A61B 5/444; A61B 5/4809; A61B 5/4812; A61B 5/4815; A61B 5/4878; A61B 5/489; A61B 5/6812; A61B 5/6814; A61B 5/6815;
(Continued)

(56) References Cited

U.S. PATENT DOCUMENTS 7,613,504 B2 * 11/2009 Rowe .................... B82Y 20/00
                                                            600/476
8,644,911 B1 *  2/2014 Panasyuk ............. A61B 5/0075
                                                            600/473
(Continued)

OTHER PUBLICATIONS

International Search Report in corresponding International Application No. PCT/US2019/061753, dated Mar. 5, 2020, 8 pgs.

*Primary Examiner* — Michael P Stafira
(74) *Attorney, Agent, or Firm* — Young Basile Hanlon & MacFarlane, P.C.

(57) ABSTRACT

Methods and systems may be used for measuring fluid status in a subcutaneous tissue space. Systems may include a wearable device or a diagnostic tool. The device may include a processor, an emitter, and a detector. The emitter and the detector are coupled to the processor. The emitter may be configured to emit a signal into a subcutaneous tissue space of a subject. The signal may be reflected by the subcutaneous tissue space. The detector may be configured to receive the reflected signal. The processor may be configured to determine a fluid status in the subcutaneous tissue space. The fluid status in the subcutaneous tissue space may be based on an energy level of the reflected signal.

18 Claims, 3 Drawing Sheets

(58) Field of Classification Search
CPC ... A61B 5/6817; A61B 5/6823; A61B 5/6832; A61B 5/684; A61B 5/6861; A61B 5/6868; A61B 5/6876; A61B 5/6879; A61B 5/6897; A61B 5/70; A61B 5/74; A61B 5/7435; A61B 6/107; A61B 6/542; A61B 8/0858; G08B 21/02; G08B 21/0423; G08B 21/0446; G08B 21/0453; G08B 21/0461; G08B 21/0476; G08B 21/0484; G08B 21/0492; G08B 25/016; G08B 2027/0138; G08B 2027/014; G08B 2027/0187; G08B 27/017; G01N 2021/0143; G01N 2021/6417; G01N 2021/6441; G01N 21/359; G01N 21/6408; G01N 21/6428; G01N 21/78; G01N 21/783; G01N 2021/0221; G01N 2201/062; G01N 2333/521; G01N 27/3273; G01N 2800/52; G01N 29/2418; G01N 33/0027; G01N 33/6893

See application file for complete search history.

(56) References Cited

U.S. PATENT DOCUMENTS

| | | | |
|---|---|---|---|
| 9,271,676 B2 | 3/2016 | Alanen et al. | |
| 2009/0326346 A1 | 12/2009 | Kracker et al. | |
| 2013/0317367 A1* | 11/2013 | Shuler | A61B 5/0075 600/473 |
| 2016/0140834 A1* | 5/2016 | Tran | A61B 7/00 340/539.11 |
| 2016/0331314 A1 | 11/2016 | Bhansali et al. | |
| 2017/0049336 A1 | 2/2017 | Hatch | |
| 2017/0303830 A1* | 10/2017 | Klein | A61B 5/6815 |

* cited by examiner

METHOD AND SYSTEM FOR MEASURING FLUID STATUS

CROSS-REFERENCE TO RELATED APPLICATION

This application claims priority to and the benefit of U.S. Provisional Application Patent Ser. No. 62/768,445, filed Nov. 16, 2018, the entire disclosure of which is hereby incorporated by reference.

TECHNICAL FIELD

This disclosure relates to a medical device.

BACKGROUND

Peripheral edema may be caused by a variety of disease states. Treatment of peripheral edema often requires continuous monitoring. Current monitoring systems are inconvenient for the patient, expensive, and fail to provide quantifiable and actionable data.

SUMMARY

Disclosed herein are implementations of methods and systems for measuring fluid status. Implementations may include a sensor assembly that is integrated into a watch band, discrete device band and/or band and module, or a module attached to a phone case. In some implementations, the sensor assembly may be integrated into a diagnostic tool.

A device, such as a wearable device or diagnostic tool, may include a processor, an emitter, and a detector. The emitter and the detector are coupled to the processor. The emitter may be configured to emit a signal into a subcutaneous tissue space of a subject. The signal may be reflected by the subcutaneous tissue space. The detector may be configured to receive the reflected signal. The processor may be configured to determine a fluid status in the subcutaneous tissue space. The fluid status in the subcutaneous tissue space may be based on an energy level of the reflected signal.

A method may be used in a wearable device to detect a fluid status in a subcutaneous tissue space of a subject. The method may include emitting a signal into the subcutaneous tissue space of a subject. The signal may be reflected by the subcutaneous tissue space. The method may include receiving the reflected signal. The method may include determining a fluid status in the subcutaneous tissue space. The fluid status in the subcutaneous tissue space may be determined based on an energy level of the reflected signal.

BRIEF DESCRIPTION OF THE DRAWINGS

The disclosure is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity.

DETAILED DESCRIPTION

Figure 1:
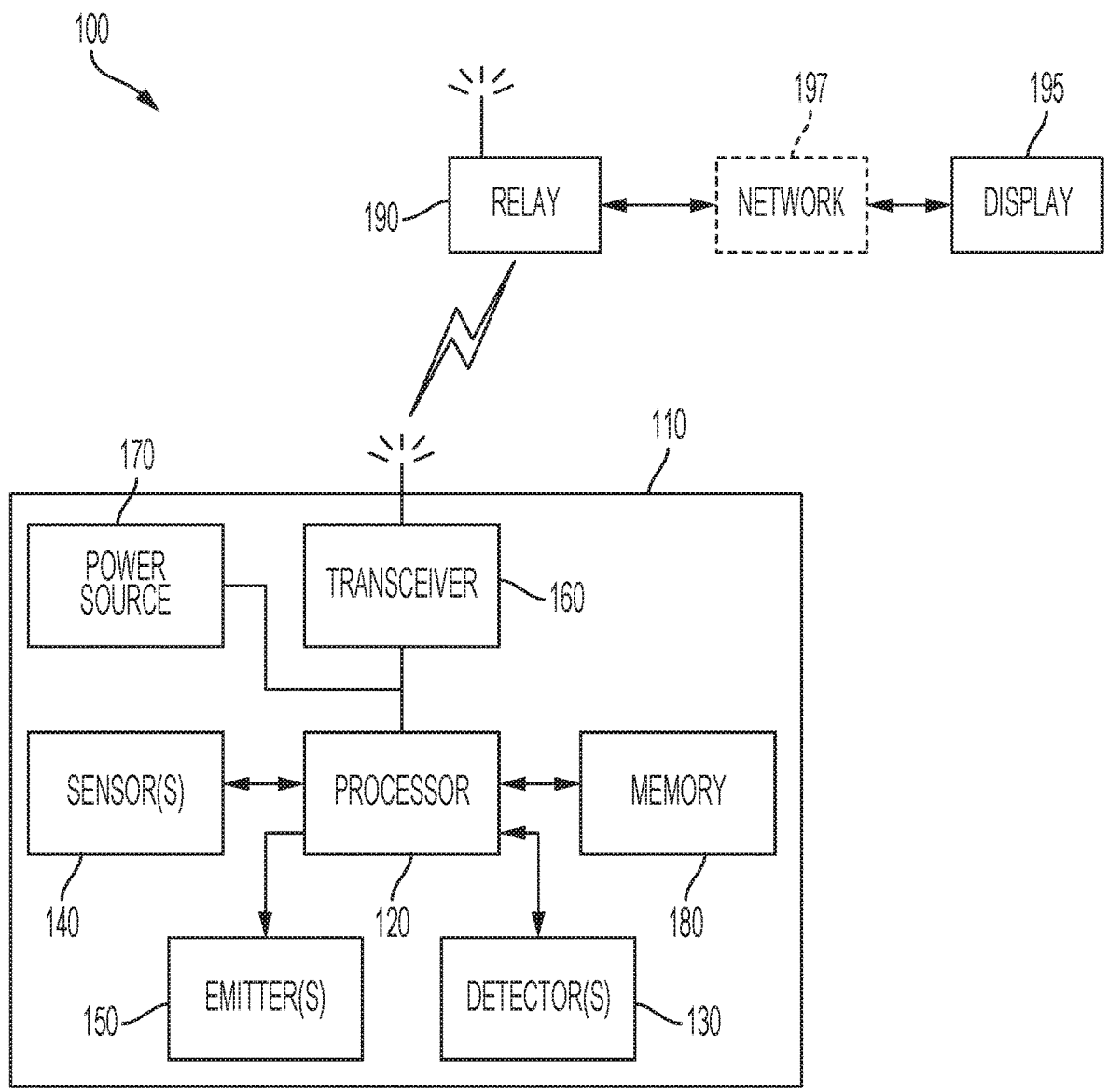
FIG. 1 is a block diagram of an example of a subcutaneous fluid detection system in accordance with embodiments of this disclosure.

FIG. 1 is a diagram of an example of a subcutaneous fluid detection system 100. The subcutaneous fluid detection system 100 may be used to detect fluid in a subcutaneous region of a subject. The subcutaneous fluid detection system 100 may be configured to quantify the detected fluid to determine a disease state of the subject. For example, the subcutaneous fluid detection system may be used to detect and manage fluid buildup associated disease states such as congestive heart failure (CHF), chronic obstructive pulmonary disease (COPD), and chronic kidney disease (CKD).

The subcutaneous fluid detection system 100 may include a device 110. The device 110 may be a wearable device or a diagnostic tool. The device 110 may be configured to be worn on a wrist, arm, leg, or any other suitable body part of a subject. The device 110 may be a watch, a bracelet, an armband, a finger ring, a headband, a wand, a probe, or any other suitable device. The device 110 includes a processor 120, one or more detectors 130, one or more sensors 140, one or more emitters 150, a transceiver 160, a power source 170, and a memory 180.

The processor 120 may include one or more processors, such as one or more special purpose processors, one or more digital signal processors, one or more microprocessors, one or more controllers, one or more microcontrollers, one or more application processors, one or more central processing units (CPU)s, one or more graphics processing units (GPU)s, one or more digital signal processors (DSP)s, one or more application specific integrated circuits (ASIC)s, one or more application specific standard products, one or more field programmable gate arrays, any other type or combination of integrated circuits, one or more state machines, or any combination thereof.

The processor 120 may be programmed to send instructions to the one or more emitters 150 and receive signals from the one or more detectors 130. The instructions may include directions or expressions for performing any method, or any portion or portions thereof, disclosed herein, and may be realized in hardware, software, or any combination thereof. For example, instructions may be implemented as information, such as a computer program, stored in memory that may be executed by a processor to perform any of the respective methods, algorithms, aspects, or combinations thereof, as described herein. Instructions, or a portion thereof, may be implemented as a special purpose processor, or circuitry, that may include specialized hardware for carrying out any of the methods, algorithms, aspects, or combinations thereof, as described herein. In some implementations, portions of the instructions may be distributed across multiple processors on a single device, on multiple devices, which may communicate directly or across a network such as a local area network, a wide area network, the Internet, or a combination thereof.

The instructions may include algorithms that may be utilized to improve signal quality, detection and timing. The processor 120 may control the timing of events. Algorithms may be used to refine signal quality received from the sensor system. This may include information from a tri-axial accelerometer, a sensor (e.g., for melanin readings to make appropriate signal adjustments), time of day, or any other sensor information. Predictive algorithms may track the information gathered so that proactive measures may be taken to maintain the health of a subject and avert crisis. General algorithms may be applied to optimize system performance, data collection and use.

The algorithms may be used to calculate the signal assessments as to positive (vs false positive) buildup of fluid. For example, once data has been taken over a large unit of subjects, an algorithm may be used to compensate for motion artifacts that may cause signal distortion at the interface between the sensor and the body. Another example would be to anticipate the impact of exercise on fluid buildup such that muscle flexing (as in the case of walking) has a tendency to purge fluid or inversely, passive sitting (as on an airplane) would cause fluid to naturally build up. In this way, the tri-axial accelerometer may be a source of information to feed such algorithms. Heart rate, respiration, and other sensor data may be factored in to algorithms to detect sub clinical edema in peripheral edema, pulmonary edema, or both. The algorithms may be tuned to be patient specific.

The one or more emitters 150 may each be a single wavelength LED emitter. In some embodiments, the one or more emitters 150 may each be a broadband emitter. Each of the one or more emitters may emit a 960 nm to 980 nm wavelength signal onto the skin of a subject. In an embodiment, the one or more emitters may emit a 970 nm wavelength signal. Each signal has a wavelength energy, and may penetrate the tissue of a subject to a depth of approximately 10 mm, for example a subcutaneous region. The signals from the one or more emitters 150 penetrate into the subcutaneous region and are reflected towards the one or more detectors 130.

The one or more detectors 130 may be any type of detector that is configured to detect light. For example, the one or more detectors 130 may include near infrared (NIR) spectrometer detectors, ultraviolet (UV) light detectors, visible light detectors, infrared spectrum detectors such as photodetectors, phototransistors, or photodiodes, or any combination thereof. The one or more detectors 130 are configured to receive the reflected light signals from the one or more emitters 150. The one or more detectors 130 are configured to measure an energy level of the received signals. The processor 120 is configured to determine a relative fluid content of the tissue based on the energy level of the received signals. For example, should the fluid level increase, less energy will be reflected to the one or more detectors 130 and the signal will decrease. Conversely, if less fluid is present, the signal level will increase. In this manner, the subcutaneous fluid detection system may measure and monitor the fluid content of a subject, for example to determine sub-clinical peripheral edema.

In an example, a method may include measuring a baseline value using the one or more detectors 130. The method may include performing periodic measurements. The periodicity and duration of the measurements may be configurable. An interval may be defined as the time between two measurements. Each measurement may be stored and tracked over time. The method may include measuring a slope of the measurements at each interval. An indication of sub-clinical peripheral edema may be determined if the slope of an interval is determined to be above a threshold.

In some embodiments, additional LED wavelength emitters may be included to support reflective pulse oximetry measurements to provide information regarding oxygen saturation that may be correlated to respiration, lung performance, or both. This information may be used to determine whether the subject has, for example, pulmonary edema. Additionally, with this signal, pulse and respiration can be captured for analysis. These additional LED wavelength emitters may be configured to emit 640 nm wavelength signals, 940 nm wavelength signals, or both. In some embodiments, additional LED wavelength emitters may be included to detect melanin content to determine skin pigmentation to support error correction for energy absorption due to skin pigmentation. In some embodiments, one or more radio frequency (RF) emitters may be included for use in the detection of fluid status in the subcutaneous tissue space. For example, a 100-1000 MHz RF emitter and corresponding detector may be used.

The one or more sensors 140 may be any type of sensor and not limited to an accelerometer, a global positioning system (GPS), a barometer, or a thermocouple. In some embodiments, a tri-axial accelerometer may be utilized to improve overall understanding the of the conditions under which measurements are taken. The accelerometer may be controlled by the processor 120. In an example, a tri-axial accelerometer may be configured to indicate the activity and posture of the subject to improve the assessment of the signal conditions and reduce motion artifacts that could impact signal quality. If the subject is active, sedentary or supine, pooling or movement of fluid may normally occur which could potentially create false positives or negatives. An activity value may be generated based on the sensor data to determine an activity status of the user to reduce false positives.

The transceiver 160 may communicate with a relay 190 via Bluetooth, Bluetooth Low Energy, WiFi, or any other wireless transmission technology. The relay 190 may be configured to receive analysis/results from the transceiver 160 of the wearable device 110 and display the analysis/results on a user interface 195. In some embodiments, the relay 190 may receive raw data from the transceiver 160 of the wearable device 110 and transmit the raw data to a network device 197. The network device 197 may be configured to determine a relative fluid content of the tissue based on the raw data associated with an energy level of the received signals. For example, should the fluid level increase, less energy will be reflected and the signal will decrease. Conversely, if less fluid is present, the signal level will increase. In this manner, the subcutaneous fluid detection system may measure and monitor the fluid content of a subject, for example to determine sub-clinical peripheral edema. The network device 197 may be configured to transmit the analysis/results to the user interface 195 for display or storage. The network device may be a cloud based system that is configured to receive, store, and process information to run predictive algorithms for review by caregivers (e.g., clinicians, etc.). The caregivers may send instructions to the wearable device 110 for further measurement information and alert the subject of actions that need to be taken. The user interface 195 may include a cell phone, tablet/PC or discrete hub device that is connected to the internet via cellular modem, WiFi, direct cable, or any other communication link.

The power source 170 may be an integrated rechargeable battery. Alternatively, the power source 170 may be a primary battery.

The memory 180 may include any computer-usable or computer-readable medium or device that can tangibly contain, store, communicate, or transport any signal or information that may be used by or in connection with any processor, for example processor 120. For example, a memory may be one or more read only memories (ROM), one or more random access memories (RAM), one or more registers, low power double data rate (LPDDR) memories, one or more cache memories, one or more semiconductor memory devices, one or more magnetic media, one or more optical media, one or more magneto-optical media, or any combination thereof. Information derived from the one or more sensors 140, processor 120, one or more detectors 130, or any combination thereof, may be stored in the memory 180 until such time as it is available to be transmitted via the transceiver 160 to the relay 190.

Figure 2:
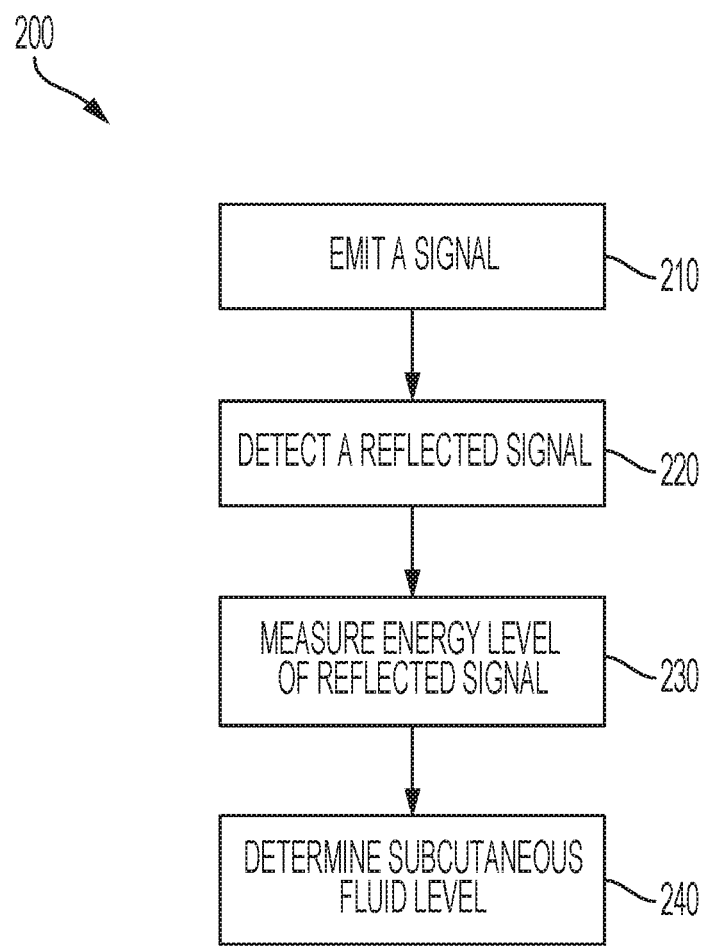
FIG. 2 is a flow diagram of an example method for detecting subcutaneous fluid.

FIG. 2 is a flow diagram of an example method 200 for detecting subcutaneous fluid. The method 200 include emitting a signal 210. The signal may be a light signal such as an LED light signal, or the signal may be an RF signal. Example LED light signals include, and are not limited to 970 nm±10 nm, 640 nm±10 nm, or 940 nm±10 nm. For example, a 660 nm and 940 nm wavelengths may be used to detect peripheral capillary oxygen saturation (SPO2) and in some instances, heart and respiration rates. Each LED light signal is emitted at a predetermined energy level. The LED light signals penetrate the skin into the subcutaneous tissue region where it is reflected back towards the skin of the subject. The method 200 includes detecting 220 the reflected signal. The method 200 includes measuring 230 an energy level of the reflected signal. The method 200 includes determining 240 a subcutaneous fluid level. The subcutaneous fluid level may be determined based on the energy level of the reflected signal.

Figure 3:
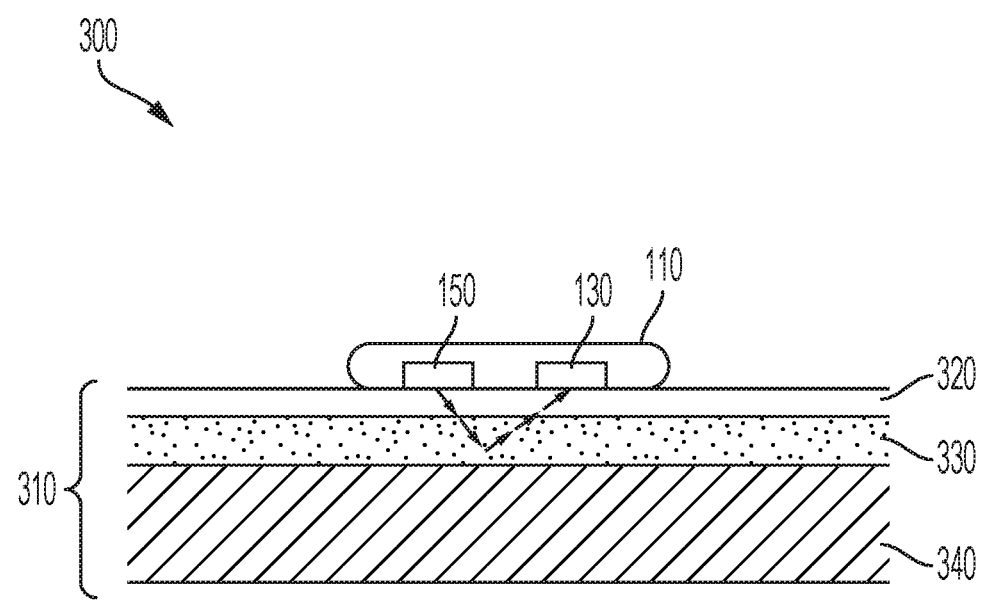
FIG. 3 is a diagram of a cross-sectional view of the subcutaneous fluid detection system of FIG. 1 on a subject in accordance with embodiments of this disclosure.

FIG. 3 is a diagram of a cross-sectional view of the device 110 of FIG. 1. Referring to FIG. 3, a cross-section of a portion of a subject body part 310 is shown. The body part may be an arm, a leg, a wrist, a finger, or any other suitable body part. As shown in FIG. 3, the body part 310 includes an epidermis (i.e., skin) layer 320, a subcutaneous tissue layer 330, and a muscle layer 340.

As shown in FIG. 3, a device 110 is placed on or in proximity to the epidermis layer 320. The emitter 150 is positioned at an angle to provide reflection of energy into the tissue to an optimal depth of 5 mm in the subcutaneous target region. In some examples, the energy may be increased to provide a depth of up to 10 mm. The emitted energy, for example 970 nm wavelength NIR light, may be reflected to the detector 130, for example an NIR Solid State Digital Spectrometer/detector. The detector 130 may be positioned at an angle to receive the reflection of energy from the tissue. In some embodiments, other wavelengths may be used, for example any wavelength from 700-970 nm. The transceiver may employ Bluetooth, Bluetooth Low Energy, WiFi or other transmission technologies as appropriate for best battery life and transmission conditions.

While the disclosure has been described in connection with certain embodiments, it is to be understood that the disclosure is not to be limited to the disclosed embodiments but, on the contrary, is intended to cover various combinations, modifications and equivalent arrangements included within the scope of the appended claims, which scope is to be accorded the broadest interpretation so as to encompass all such modifications and equivalent structures as is permitted under the law.

What is claimed is:

1. A device comprising:
   a processor;
   an emitter coupled to the processor, the emitter being configured to emit a signal into a subcutaneous tissue space of a subject, the signal being reflected by a subcutaneous tissue space; and
   a detector coupled to the processor, the detector being configured to determine an energy level based on the reflected signal;
   wherein the processor is configured to:
      periodically determine a fluid buildup in the subcutaneous tissue space based on an the energy level of the reflected signal;
      measure a rate of change of the fluid buildup; and
      determine a disease state of the subject based on the rate of change of the fluid buildup.

2. The device of claim 1, wherein the emitter is configured to emit a light emitting diode (LED) wavelength.

3. The device of claim 2, wherein the LED wavelength is 970 nm.

4. The device of claim 2, wherein the LED wavelength is 640 nm to detect a peripheral capillary oxygen saturation (SPO2).

5. The device of claim 2, wherein the LED wavelength is 940 nm to detect a pulse rate.

6. The device of claim 2, wherein the LED wavelength is a near infrared (NIR) wavelength.

7. The device of claim 1, further comprising:
   an accelerometer configured to detect activity of the subject to improve a signal condition.

8. The device of claim 7, wherein the accelerometer is further configured to detect activity of the subject to reduce motion artifacts.

9. The device of claim 1, further comprising:
   a display configured to display the determined fluid buildup.

10. A method for use in a wearable device, the method comprising:
    emitting a signal into a subcutaneous tissue space of a subject, the signal being reflected by the subcutaneous tissue space;
    periodically determining a fluid buildup in the subcutaneous tissue space based on an energy level of the reflected signal;
    measuring a rate of change of the fluid buildup; and
    determining a disease state of the subject based on the rate of change of the fluid buildup.

11. The method of claim 10, wherein the emitted signal is a light emitting diode (LED) wavelength.

12. The method of claim 11, wherein the LED wavelength is 970 nm.

13. The method of claim 11, wherein the LED wavelength is 640 nm to detect a peripheral capillary oxygen saturation (SPO2).

14. The method of claim 11, wherein the LED wavelength is 940 nm to detect a pulse rate.

15. The method of claim 11, wherein the LED wavelength is a near infrared (NIR) wavelength.

16. The method of claim 10, further comprising detecting activity of the subject to improve a signal condition.

17. The method of claim 16, wherein detecting activity of the subject is to reduce motion artifacts.

18. The method of claim 10, further comprising displaying the determined fluid buildup.

* * * * *